(12) United States Patent
Cohen et al.

(10) Patent No.: US 10,623,188 B2
(45) Date of Patent: Apr. 14, 2020

(54) SECURELY DISTRIBUTING MEDICAL PRESCRIPTIONS

(71) Applicant: Fresenius Medical Care Holdings, Inc., Waltham, MA (US)

(72) Inventors: Harvey Cohen, Newton, MA (US); Matthew Buraczenski, Holden, MA (US); Matthew O'Reilly, Brandon, FL (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 69 days.

(21) Appl. No.: 15/497,529

(22) Filed: Apr. 26, 2017

(65) Prior Publication Data

US 2018/0316505 A1 Nov. 1, 2018

(51) Int. Cl.
*H04L 29/06* (2006.01)
*A61M 1/28* (2006.01)
(Continued)

(52) U.S. Cl.
CPC ......... *H04L 9/3247* (2013.01); *A61M 1/1603* (2014.02); *A61M 1/282* (2014.02);
(Continued)

(58) Field of Classification Search
CPC ............... H04L 9/3247; H04L 63/0435; H04L 63/0442; H04L 63/0823; G16H 10/60;
(Continued)

(56) References Cited

U.S. PATENT DOCUMENTS 6,385,728 B1 5/2002 Debry
6,673,314 B1 1/2004 Burbank et al.
(Continued)

FOREIGN PATENT DOCUMENTS

DE 19845027 4/2000
DE 202012005295 9/2012
(Continued)

OTHER PUBLICATIONS

Hsu, Chien-Lung, and Chung-Fu Lu. "A security and privacy preserving e-prescription system based on smart cards." Journal of medical systems 36.6 (2012): 3637-3647. (Year: 2012).*
(Continued)

*Primary Examiner* — Michael Simitoski
(74) *Attorney, Agent, or Firm* — Fish & Richardson P.C.

(57) ABSTRACT

A medical treatment machine, such as a dialysis machine (e.g., a home dialysis machine, such as a home hemodialysis machine or a home peritoneal dialysis machine) can receive a digital prescription file that defines parameters of a medical treatment to be administered to a patient. The digital prescription file can be prepared and delivered in such a way that the medical treatment machine can confirm that the issuer (e.g., provider) of the digital prescription file is an authorized issuer without having any a priori knowledge of the particular issuer. The digital prescription file can be delivered irrespective of the inherent security (or lack thereof) of the transmission medium in a tamper-evident format using minimal resources necessary to verify the validity of the digital prescription file and its issuer. The digital prescription file may be delivered to the dialysis machine using a network cloud-based connected health system.

19 Claims, 7 Drawing Sheets

(51) Int. Cl.
*H04L 9/32* (2006.01)
*A61M 1/16* (2006.01)
*G16H 20/10* (2018.01)
*G16H 10/60* (2018.01)

(52) U.S. Cl.
CPC .............. *G16H 10/60* (2018.01); *G16H 20/10* (2018.01); *H04L 63/0435* (2013.01); *H04L 63/0442* (2013.01); *H04L 63/0823* (2013.01); *A61M 2205/3553* (2013.01); *A61M 2205/3584* (2013.01); *A61M 2205/50* (2013.01); *A61M 2205/52* (2013.01)

(58) Field of Classification Search
CPC ........... G16H 20/10; G06F 8/65; G06F 8/658; G06F 8/66; G06F 8/60; G06F 19/3418; G06F 19/3481; G06F 19/3456; G06F 19/3475; G06F 21/572; A61M 1/1603; A61M 1/282; A61M 2205/3553; A61M 2205/3584; A61M 2205/50; A61M 2205/52
USPC .......................................................... 713/176
See application file for complete search history.

(56) References Cited

U.S. PATENT DOCUMENTS

| | | | |
|---|---|---|---|
| 7,033,539 | B2 | 4/2006 | Krensky et al. |
| 7,044,927 | B2 | 5/2006 | Mueller et al. |
| 7,078,911 | B2 | 7/2006 | Cehelnik |
| 7,539,533 | B2 | 5/2009 | Tran |
| 7,699,806 | B2 | 4/2010 | Ware et al. |
| 7,981,281 | B2 | 7/2011 | Yu et al. |
| 8,190,651 | B2 | 5/2012 | Treu et al. |
| 8,313,642 | B2 | 11/2012 | Yu et al. |
| 8,315,885 | B2 | 11/2012 | Krogh et al. |
| 8,449,471 | B2 | 5/2013 | Tran |
| 8,487,881 | B2 | 7/2013 | Keenan |
| 8,529,496 | B2 | 9/2013 | Britton et al. |
| 8,549,600 | B2 | 10/2013 | Shedrinsky |
| 8,566,601 | B1 * | 10/2013 | Waters ............... H04L 9/3073 380/30 |
| 8,776,246 | B2 | 7/2014 | Allegri et al. |
| 8,871,095 | B2 | 10/2014 | Yu et al. |
| 8,905,959 | B2 | 12/2014 | Basaglia |
| 8,909,613 | B2 | 12/2014 | Treu et al. |
| 8,970,503 | B2 | 3/2015 | Christie et al. |
| 8,996,393 | B2 | 3/2015 | Sobie |
| 9,050,411 | B2 | 6/2015 | Kelly et al. |
| 9,178,891 | B2 | 11/2015 | Wang et al. |
| 9,251,310 | B2 | 2/2016 | McNally et al. |
| 9,514,283 | B2 | 12/2016 | Childers et al. |
| 9,582,645 | B2 | 2/2017 | Yu et al. |
| 9,675,745 | B2 | 6/2017 | Kelly et al. |
| 9,690,905 | B2 | 6/2017 | Yu et al. |
| 9,697,334 | B2 | 7/2017 | Yu et al. |
| 9,800,663 | B2 | 10/2017 | Arrizza |
| 9,861,733 | B2 | 1/2018 | Burbank et al. |
| 10,173,008 | B2 | 1/2019 | Simpson et al. |
| 2002/0198473 | A1 | 12/2002 | Kumar |
| 2003/0158823 | A1 * | 8/2003 | Fulton ................ G06F 21/10 705/75 |
| 2004/0088541 | A1 * | 5/2004 | Messerges .......... G06F 21/10 713/156 |
| 2004/0111294 | A1 | 6/2004 | McNally et al. |
| 2004/0117643 | A1 * | 6/2004 | Lakamp ............... G06F 21/10 713/193 |
| 2004/0193413 | A1 | 9/2004 | Wilson et al. |
| 2005/0055244 | A1 | 3/2005 | Mullan |
| 2006/0200260 | A1 | 9/2006 | Hoffberg et al. |
| 2007/0143782 | A1 * | 6/2007 | Lakamp ............... G06F 21/10 725/25 |
| 2007/0266443 | A1 * | 11/2007 | Wilson ................. G06F 21/554 726/27 |
| 2008/0114226 | A1 | 5/2008 | Music et al. |
| 2009/0259960 | A1 | 10/2009 | Steinle et al. |
| 2009/0275881 | A1 | 11/2009 | Lo et al. |
| 2009/0303204 | A1 | 12/2009 | Nasiri |
| 2010/0066676 | A1 | 3/2010 | Kramer et al. |
| 2010/0114639 | A1 | 5/2010 | Leiendecker et al. |
| 2010/0138534 | A1 | 6/2010 | Mutnum et al. |
| 2010/0200506 | A1 | 8/2010 | Ware |
| 2011/0093294 | A1 | 4/2011 | Elahi et al. |
| 2011/0157480 | A1 | 6/2011 | Curl |
| 2011/0164163 | A1 | 7/2011 | Bilbrey et al. |
| 2012/0003933 | A1 | 1/2012 | Baker et al. |
| 2012/0138533 | A1 | 6/2012 | Curtis et al. |
| 2013/0018355 | A1 | 1/2013 | Brand et al. |
| 2013/0138452 | A1 | 5/2013 | Cork et al. |
| 2013/0141329 | A1 | 6/2013 | Halbert et al. |
| 2013/0249855 | A1 | 9/2013 | Zhang |
| 2013/0310726 | A1 | 11/2013 | Miller et al. |
| 2013/0318357 | A1 * | 11/2013 | Abraham ............. G06F 21/57 713/176 |
| 2013/0346102 | A1 | 12/2013 | Yu et al. |
| 2014/0006510 | A1 | 1/2014 | Hamilton et al. |
| 2014/0121845 | A1 | 5/2014 | Mueller |
| 2014/0188516 | A1 | 7/2014 | Kamen |
| 2014/0266983 | A1 | 9/2014 | Christensen |
| 2014/0267003 | A1 | 9/2014 | Wang |
| 2014/0276375 | A1 | 9/2014 | Minkus |
| 2014/0288947 | A1 | 9/2014 | Simpson et al. |
| 2015/0011970 | A1 | 1/2015 | Kamen et al. |
| 2015/0095041 | A1 | 4/2015 | Kim |
| 2015/0253860 | A1 | 9/2015 | Merics et al. |
| 2015/0370973 | A1 | 12/2015 | Jones |
| 2016/0206800 | A1 | 7/2016 | Tanenbaum et al. |
| 2016/0261974 | A1 | 9/2016 | Arrizza |
| 2017/0076069 | A1 | 3/2017 | Moissl et al. |
| 2017/0087290 | A1 | 3/2017 | Medina et al. |

FOREIGN PATENT DOCUMENTS

| | | | |
|---|---|---|---|
| DE | 102012020945 | | 4/2014 |
| EP | 2237131 | | 10/2010 |
| EP | 2145451 | | 12/2012 |
| GB | 2368436 A | * | 10/2000 ............. G06F 17/60 |
| WO | WO 2008/042219 | | 4/2008 |
| WO | WO 2008/144325 | | 11/2008 |
| WO | WO 2011/028261 | | 3/2011 |
| WO | WO 2014/004448 | | 1/2014 |
| WO | WO 2014/134229 | | 9/2015 |

OTHER PUBLICATIONS

International Preliminary Report on Patentability in Application No. PCT/US2018/027857, dated Oct. 29, 2019, 10 pages.
Application Document, Bluetooth Secure Simple Pairing Using NFC, Bluetooth Special Interest Group, NFC Forum, NFCForum-AD-BTSSP-1.0, Oct. 18, 2011, 32 pages.
International Preliminary Report on Patentability in Application No. PCT/US2017/042111, dated Feb. 5, 2019, 13 pages.
International Search Report and Written Opinion in Application No. PCT/US2017/042111, dated Nov. 15, 2017, 21 pages (with English translation).
International Search Report and Written Opinion in International Application No. PCT/US2018/027857, dated Jun. 29, 2018, 17 pages.
Invitation to Pay Additional Fees in International Application No. PCT/US2017/042111, dated Sep. 15, 2017, 17 pages.
Jung et al., "Interoperability between Medical Devices using Near Field Communication", IEEE, Jun. 24, 2013, pp. 1-4.

* cited by examiner

SECURELY DISTRIBUTING MEDICAL PRESCRIPTIONS

TECHNICAL FIELD

This disclosure relates to distributing medical prescriptions.

BACKGROUND

Medical treatment machines can be designed to aid in the diagnosis, monitoring, and/or treatment of a variety of medical conditions. One example of a medical treatment machine is a dialysis machine. Dialysis is a treatment used to support a patient with insufficient renal function. The two principal dialysis methods are hemodialysis and peritoneal dialysis. During hemodialysis ("HD"), the patient's blood is passed through a dialyzer of the dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Automated PD machines called PD cyclers are designed to control the entire PD process so that it can be performed at home usually overnight without clinical staff in attendance. This process is termed continuous cycler-assisted PD ("CCPD"). Many PD cyclers are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect, a method includes receiving, by a medical treatment machine, a digital prescription file that is encrypted using a public key. The digital prescription file is digitally signed by an issuer of the digital prescription file using a private key that corresponds to the issuer. The method also includes decrypting the digital prescription file using a private key that corresponds to the public key. The private key is accessible by the medical treatment machine. The method also includes identifying the issuer of the digital prescription file using the decrypted digital prescription file. The method also includes determining that the issuer of the digital prescription file is an authorized issuer by verifying that a certificate that corresponds to i) the issuer, and ii) the private key used to digitally sign the digital prescription file, is digitally signed by a trusted authority service. The method also includes verifying a digital signature on the digital prescription file using a public key that corresponds to the authorized issuer to confirm that the issuer is the authorized issuer. In some example, in this way, any authorized issuer can securely issue digital prescription files consumable by any authorized medical treatment machine, without requiring that either party possesses any a priori knowledge of the other.

Implementations can include one or more of the following features.

In some implementations, the private key that corresponds to the public key is pre-loaded on the medical treatment machine.

In some implementations, the public key that corresponds to the authorized issuer is provided by the trusted authority service.

In some implementations, the trusted authority service is a certificate authority. In some implementations, the method includes performing a dialysis treatment based on the digital prescription file.

In some implementations, the digital prescription file is encrypted by the issuer without the issuer knowing additional information (e.g., unique information) about the medical treatment machine.

In some implementations, the digital prescription file is decrypted by the medical treatment machine before the medical treatment machine learns the identity of the issuer.

In some implementations, the method includes receiving, by the medical treatment machine, the certificate that corresponds to the issuer. The certificate includes a public key that corresponds to the i) issuer, and ii) the private key that corresponds to the issuer, and is digitally signed by the trusted authority service using a private key that corresponds to the trusted authority service. The method also includes verifying a digital signature on the certificate using a public key that corresponds to the trusted authority service to confirm that the public key included in the certificate corresponds to an authorized issuer.

In some implementations, the method includes determining that the trusted authority service is trusted to verify identities of issuers and certify ownership of public keys corresponding to the issuers.

In some implementations, a certificate that includes a public key that corresponds to the trusted authority service is stored in the medical treatment machine.

In some implementations, a certificate that includes a public key that corresponds to the trusted authority service is received by the medical treatment machine in a manner that indicates that the trusted authority service is a trusted authorizer of prescription issuers.

In some implementations, the certificate that corresponds to the issuer is provided by the trusted authority service after the trusted authority service verifies the identity of the issuer and certifies that the issuer is an authorized issuer.

In another aspect, a method includes receiving, by a medical treatment machine, a digital prescription file that is encrypted using a public key. The digital prescription file is digitally signed by an issuer of the digital prescription file using a private key that corresponds to the issuer. The method also includes receiving, by the medical treatment machine, a certificate that includes a public key that corresponds to the issuer. The certificate is digitally signed by a trusted authority service using a private key that corresponds to the trusted authority service. The method also includes decrypting the digital prescription file using a private key that corresponds to the public key. The private key is accessible by the medical treatment machine. The method also includes verifying a digital signature on the certificate using a public key that corresponds to the trusted authority service to confirm that the public key included in the certificate corresponds to an authorized issuer. The method also includes verifying a digital signature on the digital prescription file using the public key included in the certificate to confirm that the issuer is the authorized issuer.

Implementations can include one or more of the following features.

In some implementations, the issuer is confirmed to be the authorized issuer without the medical treatment machine knowing additional information (e.g., specific information) about the issuer.

In another aspect, a medical system includes a medical device, data storage, and a processor configured for receiving a digital prescription file that is encrypted using a public key. The digital prescription file is digitally signed by an issuer of the digital prescription file using a private key that corresponds to the issuer. The processor is also configured for decrypting the digital prescription file using a private key that corresponds to the public key. The private key is accessible by the medical device. The processor is also configured for identifying the issuer of the decrypted digital prescription file using the digital prescription file. The processor is also configured for determining that the issuer of the digital prescription file is an authorized issuer by verifying that a certificate that corresponds to i) the issuer, and ii) the private key used to digitally sign the digital prescription file is digitally signed by a trusted authority service. The processor is also configured for verifying a digital signature on the digital prescription file using a public key that corresponds to the authorized issuer to confirm that the issuer is the authorized issuer.

Implementations can include one or more of the following features.

In some implementations, the medical device is a dialysis machine that is configured to perform a dialysis treatment based on the digital prescription file.

In some implementations, the dialysis machine includes a home dialysis machine ("HDM").

In some implementations, the dialysis machine includes a peritoneal dialysis ("PD") machine.

In some implementations, the dialysis machine includes a hemodialysis ("HD") machine.

In another aspect, a connected health system includes a cloud-based application that facilitates data transfer between components of the system. The cloud-based application also includes a dialysis machine and a gateway device in communication with the dialysis machine and the cloud-based application. The gateway device is configured to receive data from the cloud-based application and provide the data to the dialysis machine. The connected health system also includes data storage. The connected health system also includes a processor configured for receiving, via the cloud-based application, a digital prescription file that is encrypted using a public key. The digital prescription file is digitally signed by an issuer of the digital prescription file using a private key that corresponds to the issuer. The processor is also configured for decrypting the digital prescription file using a private key that corresponds to the public key. The private key is accessible by the dialysis machine. The processor is also configured for identifying the issuer of the decrypted digital prescription file using the digital prescription file. The processor is also configured for determining that the issuer of the digital prescription file is an authorized issuer by verifying that a certificate that corresponds to i) the issuer, and ii) the private key used to digitally sign the digital prescription file, is digitally signed by a trusted authority service. The processor is also configured for verifying a digital signature on the digital prescription file using a public key that corresponds to the authorized issuer to confirm that the issuer is the authorized issuer.

Implementations can include one or more of the following advantages.

In some implementations, the prescription file can be generated and delivered digitally. In some implementations, the digital prescription file can be signed digitally in a non-forgeable manner that uniquely identifies both the digital prescription file and the issuer of the digital prescription file. In some implementations, the certificate that includes the public key that corresponds to the issuer (e.g., the certificate of the issuer) may itself be embedded in the digitally signed digital prescription file. For example, in some implementations, the certificate of the issuer does not require separate and/or secure delivery. In some implementations, the digital prescription file may be delivered using any digital medium and may use either secure or insecure means (e.g., because the nature of the digital signature can expose attempts to modify the file in transit).

In some implementations, a receiver of the digital prescription file (e.g., the dialysis machine) requires no prior knowledge of the existence of the particular issuer. For example, in some implementations, any issuer, known or unknown by the receiver, may issue a valid (e.g., verifiable) digital prescription file. In some implementations, the issuer of the digital prescription file requires no prior knowledge of the particular receiver (e.g., the particular dialysis machine). For example, in some implementations, any dialysis machine may consume any prescription file without the issuer having prior knowledge of the existence of the particular dialysis machine.

In some implementations, the certificate that includes the public key that corresponds to the authority service (e.g., the certificate of the certificate authority) is pre-loaded on the dialysis machine or received by the dialysis machine. In some implementations, the certificate authority is authorized to sign certificates (e.g., issuer certificates) for issuers who are approved to provide digital prescription files. In some implementations, the dialysis machine may use the signer of the issuer's certificate (e.g., the certificate authority) as the sole authorization and indication to determine that the issuer (e.g., the signer) of the digital prescription file is an authorized issuer.

In some implementations, by using a certificate authority to verify identities of issuers, issuers need not be authorized one-by-one by the dialysis machine, and in turn, digital prescription files can be securely delivered without the original source or the recipient being known ahead of time (e.g., irrespective of the particular issuer or the particular recipient dialysis machine).

In some implementations, by encrypting the digital prescription file according to a public-key cryptography scheme, only recipients who possess the corresponding private key can decrypt the file and view its original contents. Further, by employing a digital signature, the recipient can confirm that the issuer is in fact who they claim to be and the file was not modified since it was signed by the issuer.

Other aspects, features, and advantages of the subject matter included herein will be apparent from the description and drawings, and from the claims.

DESCRIPTION OF DRAWINGS

Like reference symbols in the various drawings indicate like elements.

DETAILED DESCRIPTION

Figure 1:
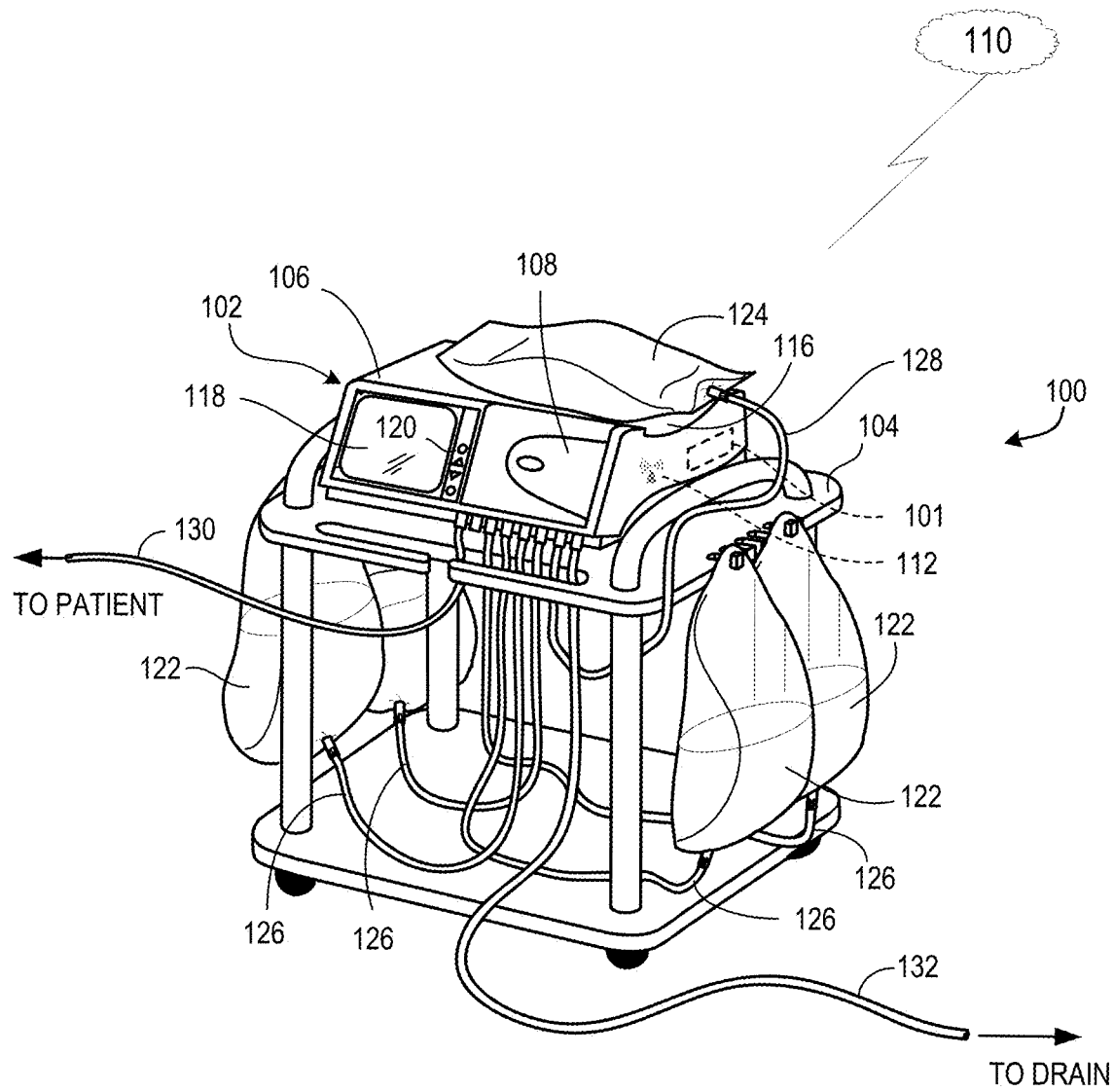
FIG. 1 is a front perspective view of a peritoneal dialysis machine that is connected to a network.

Described herein is a technique for allowing digital prescription files to be transmitted to and from entities who have no a priori knowledge of one another, in some cases irrespective of the inherent security (or lack thereof) of the transmission medium, in a tamper-evident format, using minimal resources necessary to verify the validity of the digital prescription file and its issuer. The technique also enables additional security measures to be supplemented using the technique, including but not limited to encryption and real-time authentication and/or authorization, without inherently altering the technique. The term "digital prescription file" may be understood to include and refer to a set of programming instructions that may be used to carry out a medical treatment that has been medically prescribed by an appropriate doctor or other medical practitioner. In some implementations, the term "prescription" may be understood to refer to what the doctor actually prescribes to the patient and may be captured in the patient's electronic health record (EHR). This prescription may be appropriately translated, formatted, encrypted and/or otherwise converted into the digital prescription file that contains the program and/or instruction sets for the medical device (e.g., the dialysis machine) to carry out the prescribed treatment.

Cryptographic systems and methods can be employed to encrypt information and/or authenticate a source of information. For example, a file that includes sensitive information (e.g., a digital prescription file) may be encrypted and/or digitally signed before being sent to a destination. The encryption can ensure that the communication is kept integral and confidential during transit, while a digital signature can ensure the integrity of the contents without requiring decryption, and ensures that the source can be properly authenticated by the recipient.

When a file is encrypted, the information included in the original file called "plaintext" (e.g., the prescription) is transformed into a different form according to a cryptographic algorithm. For example, a file that includes the text string (e.g., "Hello World") may be transformed into a format called "cyphertext" (e.g., "3B582EC3D-210A12C38541DE975672B0272B9345") by encrypting the file with a key. A person who intercepts the encrypted file will only be able to see the cyphertext and not the original plaintext. In order to convert the cyphertext back to plaintext, a recipient typically must be in possession of a key that corresponds to the key used to encrypt the file. The key in possession of the recipient can be applied to the cyphertext to decrypt the file, thereby reproducing the plaintext. In this way, the issuer of encrypted information can ensure that only those who possess the correct key can view the sensitive information.

In addition to being encrypted, the file may also be digitally signed by the issuer. When the file is digitally signed, the plaintext is hashed (e.g., a hash algorithm is applied to the data) in order to produce a digest (e.g., sometimes referred to as a hash). The digest is then encrypted using a private key that corresponds to the issuer (e.g., a different key than the one described above with respect to the decryption), thereby producing a digital signature. The recipient can verify the signature by: i) computing the digest of the plaintext; ii) verifying (e.g., decrypting) the digital signature using a public key that corresponds to the issuer's private key in order to reproduce the digest; and iii) comparing the computed digest with the reproduced (e.g., decrypted) digest. If the computed digest and the decrypted digest are equal, it can be confirmed that: i) the file was unmodified since being signed; and ii) the signer (e.g., the issuer) performed the signature operation.

Thus, by employing a digital signature, the recipient can confirm that the issuer is in fact who they claim to be and the file was not modified since it was signed by the issuer.

A medical treatment machine such as a dialysis machine (e.g., a home dialysis machine ("HDM")) can be configured to receive a digital prescription file that defines parameters of a medical treatment (e.g., a dialysis treatment) to be administered to a patient. The digital prescription file can be prepared and delivered in such a way that the medical treatment machine can confirm that the issuer of the digital prescription file is an authorized issuer without having any a priori knowledge of the particular issuer. For example, the digital prescription file may be digitally signed by the issuer using a private key unique to the issuer. The signed digital prescription file is delivered to the medical treatment machine via a secured or unsecured medium. The medical treatment machine reads the digital prescription file, identifies the purported issuer, and confirms that the purported issuer is an authorized issuer.

In some implementations, the medical treatment machine confirms that the purported issuer is an authorized issuer by verifying that a certificate that corresponds to the issuer (and, e.g., that corresponds to the issuer's private key used to digitally sign the digital prescription file) is digitally signed by a trusted authority service (e.g., a known authorizer of issuers responsible for verifying identities of issuers and certifying ownership of public keys corresponding to such issuers), as described in more detail below.

In some implementations, an issuer may communicate with a certificate authority (e.g., a certificate authority that is trusted by the medical treatment machine to authorize issuers) ahead of time to obtain authorized status. For example, the issuer may provide their public key to the certificate authority for verification, and the certificate authority can verify the identity of the issuer and provide an issuer certificate in return. The issuer certificate, which includes the issuer's public key, is digitally signed by the certificate authority using a private key of the certificate authority. The issuer certificate can be provided to the medical treatment machine along with the digital prescription file. The certificate authority's public key, which is accessible by the medical treatment machine, can be used to verify that the issuer certificate was in fact signed by the certificate authority. Because the certificate authority is a trusted entity, the medical treatment machine can treat the information included in the issuer's certificate (e.g., the issuer's public key) as trusted. The medical treatment machine may then use the issuer's public key to confirm that the digital prescription file was, in fact, signed by the authorized issuer and was not modified since being signed. In this way, issuers need not be authorized individually by the medical treatment machine, and in turn, digital prescription files can be securely delivered without the original source or the recipient being known ahead of time (e.g., irrespective of the particular issuer or the particular recipient medical treatment machine).

In some implementations, the medical treatment machine can confirm that the purported issuer is an authorized issuer by communicating with a third-party authority service, which can provide the medical treatment machine with a public key known to correspond to the authorized issuer. The medical treatment machine may then use the public key to confirm that the digital prescription file was, in fact, signed by the authorized issuer and was not modified once signed.

In addition to being digitally signed by the issuer, the digital prescription file can be encrypted using a public key that is known to the issuer. The public key has a corresponding private key that can be pre-loaded on the medical treatment machine. In some implementations, the private key is available to the medical treatment machine for download from a trusted source. In some implementations, the private key is available for use by the medical treatment machine by sending the encrypted digital prescription file to a trusted processor for decryption and receiving the decrypted file in return. Upon receipt of the encrypted digital prescription file, the medical treatment machine can use the corresponding private key to decrypt the digital prescription file. Because the private key can be pre-loaded on all medical treatment machines (e.g., at the time of manufacture or at any time thereafter), digital prescription files can be securely delivered to any medical treatment machine and decrypted by the medical treatment machine without restriction. In some implementations, the digital prescription file is encrypted with a symmetric key, which itself is then encrypted using the public key.

In some implementations, the medical treatment machine may be a peritoneal dialysis machine. FIG. 1 shows an example of a PD system 100 that is configured to receive a digital prescription file. In some implementations, the PD system 100 is configured for use at a patient's home (e.g., a home PD system). The PD system 100 includes a PD machine (also referred to as a PD cycler) 102 seated on a cart 104. The PD machine 102 includes a housing 106, a door 108, and a cassette interface that contacts a disposable PD cassette when the cassette is disposed within a cassette compartment formed between the cassette interface and the closed door 108. A heater tray 116 is positioned on top of the housing 106. The heater tray 116 is sized and shaped to accommodate a bag of dialysate (e.g., a 5-liter bag of dialysate). The PD machine 102 also includes a user interface such as a touch screen 118 and control panel 120 that can be operated by a user (e.g., a caregiver or a patient) to allow, for example, set up, initiation, and/or termination of a PD treatment.

Dialysate bags 122 are suspended from fingers on the sides of the cart 104, and a heater bag 124 is positioned in the heater tray 116. The dialysate bags 122 and the heater bag 124 are connected to the cassette via dialysate bag lines 126 and a heater bag line 128, respectively. The dialysate bag lines 126 can be used to pass dialysate from dialysate bags 122 to the cassette during use, and the heater bag line 128 can be used to pass dialysate back and forth between the cassette and the heater bag 124 during use. In addition, a patient line 130 and a drain line 132 are connected to the cassette. The patient line 130 can be connected to a patient's abdomen via a catheter and can be used to pass dialysate back and forth between the cassette and the patient's peritoneal cavity during use. The drain line 132 can be connected to a drain or drain receptacle and can be used to pass dialysate from the cassette to the drain or drain receptacle during use.

The touch screen 118 and the control panel 120 allow an operator to input various treatment parameters to the PD machine 102 and to otherwise control the PD machine 102. In addition, the touch screen 118 servers as a display. The touch screen 118 functions to provide information to the patient and the operator of the PD system 100. For example, the touch screen 118 may display information related to a dialysis treatment to be applied to the patient, including information related to a prescription, as described in more detail below.

The PD machine 102 includes a processing module 101 that resides inside the PD machine 102 and which is configured to communicate with the touch screen 118 and the control panel 120. The processing module 101 is configured to receive data from the touch screen 118 and the control panel 120 and control the PD machine 102 based on the received data. For example, the processing module 101 can adjust the operating parameters of the PD machine 102. In some implementations, the processing module 101 is an MPC823 PowerPC device manufactured by Motorola, Inc.

The PD machine 102 is configured to connect to a network 110. The PD machine 102 includes a transceiver 112 that is configured to facilitate the connection to the network 110. Other medical devices (e.g., peripheral devices or monitors, other dialysis machines, etc.) may be configured to connect to the network 110 and communicate with the PD machine 102. Similarly, one or more remote entities, such as issuers of digital prescription files and/or authority services tasked with verifying identities of issuers and certifying ownership of public keys corresponding to the issuers, may be able to connect to the network 110 and communicate with the PD machine 102 in order to provide digital prescriptions for implementing on the PD machine 102, digital certificates, and/or public keys usable to verify digital signatures. Such connections to the network 110 may be made through a cloud-based service (e.g., a Connected Health Service ("CHS")), as described in more detail below.

Figure 2:
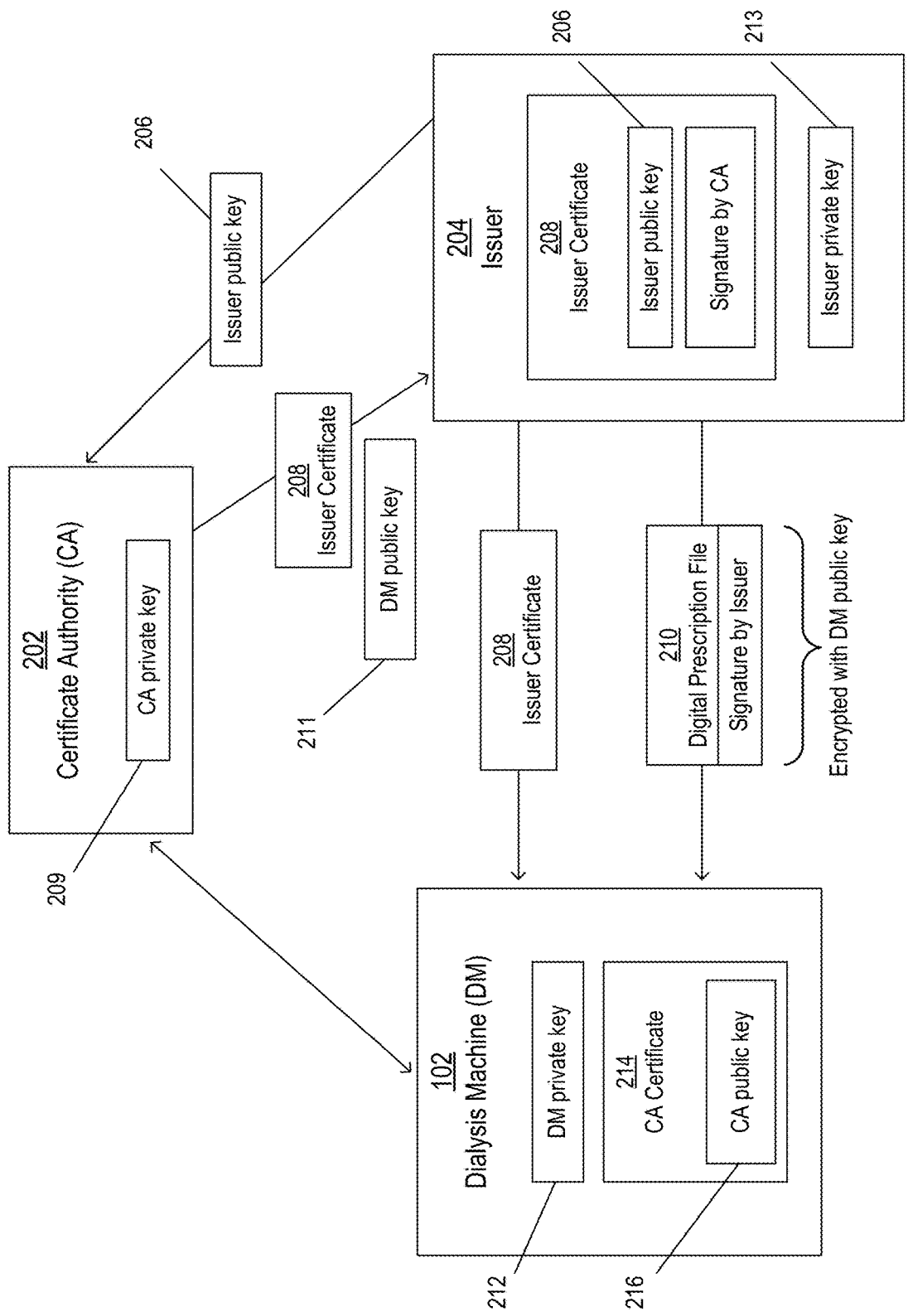
FIG. 2 illustrates a system for communicating information between the dialysis machine, a certificate authority, and an issuer.

FIG. 2 illustrates a system for communicating information between the dialysis machine ("DM") 102, a certificate authority ("CA") 202, and an issuer 204. The CA 202 may be a third party that is trusted by the DM 102 to authorize and authenticate the identity of the issuer 204, and the issuer 204 may be any entity that seeks to provide prescriptions to the DM 102, such as a hospital or a clinic.

Before providing a prescription to the DM 102, the issuer 204 may communicate with the CA 202 to verify its identity and obtain authorized status. The CA 202 is tasked with confirming that the issuer 204 is in fact who they say they are, and also verifying that the issuer 204 has the authority, trust, and/or qualifications to issue prescriptions to the DM 102. Once it is determined by the CA 202 that the issuer 204 is authorized to issue prescriptions, the issuer 204 provides an issuer public key 206 to the CA 202. After verifying that the issuer public key 206 does in fact correspond to the issuer 204, the CA 202 provides an issuer certificate 208 to the issuer 204. The issuer certificate 208 includes the issuer public key 206 and is digitally signed by the CA 202 using a private key (e.g., a CA private key 209) that corresponds to the CA 202. The issuer 204, now authorized, is able to provide prescriptions to the DM 102.

The issuer 204 may create a prescription that is to be provided to the DM 102. The prescription may be defined in plaintext that is readable by the DM 102. For example, the DM 102 may read a set of instructions included in the plaintext and execute functions based on the instructions. The prescription may include instructions such as the flow rate to be employed during a fill phase of a cycle, a flow rate to be employed during a drain phase of a cycle, a number of rounds of treatment to be performed, a number of cycles to be performed per treatment round, a fill volume to be used for each cycle, and a dwell time to be used for each cycle, among others.

The prescription is included as part of a digital prescription file 210 that is provided to the DM 102. To protect the privacy of the information included therein, the digital prescription file 210 may be encrypted using a public key (e.g., a DM public key 211) that corresponds to the DM 102 and other DMs. In some implementations, the DM public key 211 is known and accessible to any issuer 204 who seeks to provide encrypted information to the DM 102. In some implementations, the CA 202 can provide the DM public key 211 to the issuer 204 after verifying the identity of the issuer 204. ADM private key 212 that corresponds to the DM public key 211 may be stored on the DM 102 or otherwise accessible by the DM 102. For example, the DM private key 212 may be stored on the DM 102 at the time of manufacture of the DM 102 or any time thereafter. After receiving the digital prescription file 210, the DM 102 can use the DM private key 212 to decrypt the digital prescription file 210 and obtain the plaintext of the prescription. The decrypted digital prescription file can also be used by the DM 102 to identify the particular issuer 204 of the digital prescription file 210.

The DM public key 211 and the DM private key 212 correspond to not only the particular DM 102, but also any related DM that is included as part of the system. That is, the DM private key 212 can be stored on all related DMs and can be used to decrypt information that is encrypted using the DM public key 211. In this way, digital prescription files 210 can be securely delivered by the issuer 204 without the particular recipient DM being known ahead of time, and can be decrypted by the DM 102 before the DM 102 learns the identity of the issuer 204 (or, in some cases, without the DM 102 ever learning the particular identity of the issuer 204, as described in more detail below).

Because the DM public key 211 may be widely known (e.g., including to issuers who are not authorized to provide prescriptions to the DM 102), received encrypted digital prescription files 210 are not necessarily safe to implement without further verification. For example, someone who is not authorized to provide prescriptions may obtain the DM public key 211, create a prescription that includes dangerous instructions, encrypt the prescription using the DM public key 211, and provide the encrypted prescription to a DM. To prevent such a situation, the DM 102 is configured to verify the identity of the issuer 204 before trusting the digital prescription file 210.

In addition to being encrypted, the digital prescription file 210 is digitally signed with a private key (e.g., an issuer private key 213) that corresponds to the issuer 204. The digital signature can be verified using the issuer public key 206, which corresponds to the issuer private key 213. If the digital signature is verified, it is confirmed that i) the digital prescription file 210 was unmodified since being signed, and ii) the signer (e.g., the issuer 204) performed the signature operation. Further information about how the digital signature is verified using the issuer public key 206 is described below with respect to FIG. 3B.

In some implementations (e.g., implementations in which the digital prescription file 210 is encrypted), the DM 102 identifies the issuer 204 of the digital prescription file 210 using the decrypted digital prescription file. The decrypted digital prescription file may include identification information related to the particular issuer 204. The DM 102 then communicates with (e.g., queries) the CA 202 to obtain the issuer public key 206 that corresponds to the issuer 204. For example, after decrypting the digital prescription file 210 and identifying the purported issuer 204, the DM 102 may ask the CA 202 whether the purported issuer 204 is an authorized issuer (e.g., an issuer who is authorized to provide prescriptions). If the purported issuer 204 is authorized to provide prescriptions, the CA 202 can provide the issuer public key 206 that corresponds to the issuer 204 who is known to be authorized. The DM 102 can use the issuer public key 206 to confirm that the digital prescription file 210 was in fact signed by the authorized issuer 204 and was not modified since being signed, as described in more detail below.

In some implementations, the DM 102 may obtain the issuer public key 206, confirm that the purported issuer 204 is authorized to provide prescriptions, and verify the digital signature without communicating (e.g., concurrently communicating) with the CA 202. This type of verification may be performed if the DM 102 is unable to communicate with the CA 202 (e.g., due to lack of Internet access).

As described above, before providing prescriptions to the DM 102, the issuer 204 may obtain authorized status by communicating with the CA 202. Once the issuer 204 is authorized, the CA 202 provides an issuer certificate 208 to the issuer 204. The issuer certificate 208 includes the issuer public key 206 and is digitally signed by the CA 202 using the CA private key 209. The issuer certificate 208 can be provided to the DM 102 along with the digital prescription file 210.

A CA certificate 214 is stored on the DM 102. The CA certificate 214 may be provided to the DM 102 before prescriptions are received (e.g., at the time of manufacture of the DM 102 or any time thereafter). In some implementations, the CA certificate 214 is stored on the DM 102 or stored in a location that is accessible by the DM 102 (e.g., via the network 110). In some implementations, the CA certificate 214 is received by the DM 102 in a manner that indicates that the CA is a trusted authorizer of prescriptions issues. For example, the CA certificate 214 may be delivered via a secure channel that is only accessible by those who are trusted authorizers of prescription issuers. In some implementations, the CA certificate 214 is stored in a data repository that includes information related to one or more trusted certificate authorities. The CA certificate 214 includes a public key (e.g., a CA public key 216) that corresponds to the CA 202. The digital signature on the issuer certificate 208 can be verified using the CA public key 216. If the digital signature is verified, it is confirmed that i) the issuer certificate 208 was unmodified since being signed by the CA 202, and ii) the signer (e.g., the CA 202) performed the signature operation. Because the CA 202 is a trusted entity, the DM 102 can treat the information included in the issuer certificate 208 (e.g., the issuer public key 206) as trusted. The DM 102 may then use the issuer public key 206 included in the issuer certificate 208 to verify the signature on the digital prescription file, thereby confirming that the digital prescription file 210 was in fact signed by the issuer 204 (e.g., who is now known to be trusted and authorized) and was not modified since being signed. The DM 102 may then implement the treatment defined by the prescription.

The digital prescription file 210 can include a prescription, which in some implementations can be in plaintext format. The prescription is usable by the dialysis system 100 to perform a dialysis treatment. The digital prescription file 210 can include patient attributes such as a Patient ID, a serial number of a cycler to be used, information related to a date and time at which the cycler was assigned to the patient, an ID associated with the patient's provider (e.g., issuer), an ID associated with the patient's clinic, the patient's first and last name, a minimum peritoneal volume of the patient, and a maximum peritoneal volume of the patient. In some implementations, the digital prescription file 210 can contain multiple prescriptions (e.g., six) for the patient. The digital prescription file 210 can include a date/time stamp identifying a time at which each prescription was created and/or assigned to the patient.

The digital prescription file 210 also includes attributes related to each prescription. For example, the prescription may have attributes related to a prescription sequence ID, a prescription ID, a name (e.g., to be displayed on the DM 102), a type for a disposable line set to be used when providing the treatment (e.g., "low feature," "medium feature," "high feature"), a quality of a catheter to be used when providing the treatment (e.g., "slow," "average," "fast"), a flow rate to be used during the fill phase of a cycle, a flow rate to be used during the drain phase of a cycle, and a requested time at which the treatment is to end.

Within a prescription, a patient can have one or more rounds of treatment. Each round can have one cycle or multiple repeating cycles. Repeating cycles within a particular round may have the same settings. In some implementations, the digital prescription file 210 includes attributes related to the particular prescription round and/or cycle, such as a prescription round ID (e.g., giving the position of the round in the treatment sequence), a number of cycles included in a particular round, a cycle type code (e.g., "cycler," "manual," "PD+," "last fill"), a requested fill volume for each cycle in the round, a requested dwell time for each cycle in the round, an expected ultrafiltration volume for each cycle in the round, a drain mode (e.g., "standard," "complete"), and a requested drain volume for each cycle in the round. In some implementations, the digital prescription file 210 also includes attributes related to a type of bag prescribed for a particular treatment.

Figure 3A:
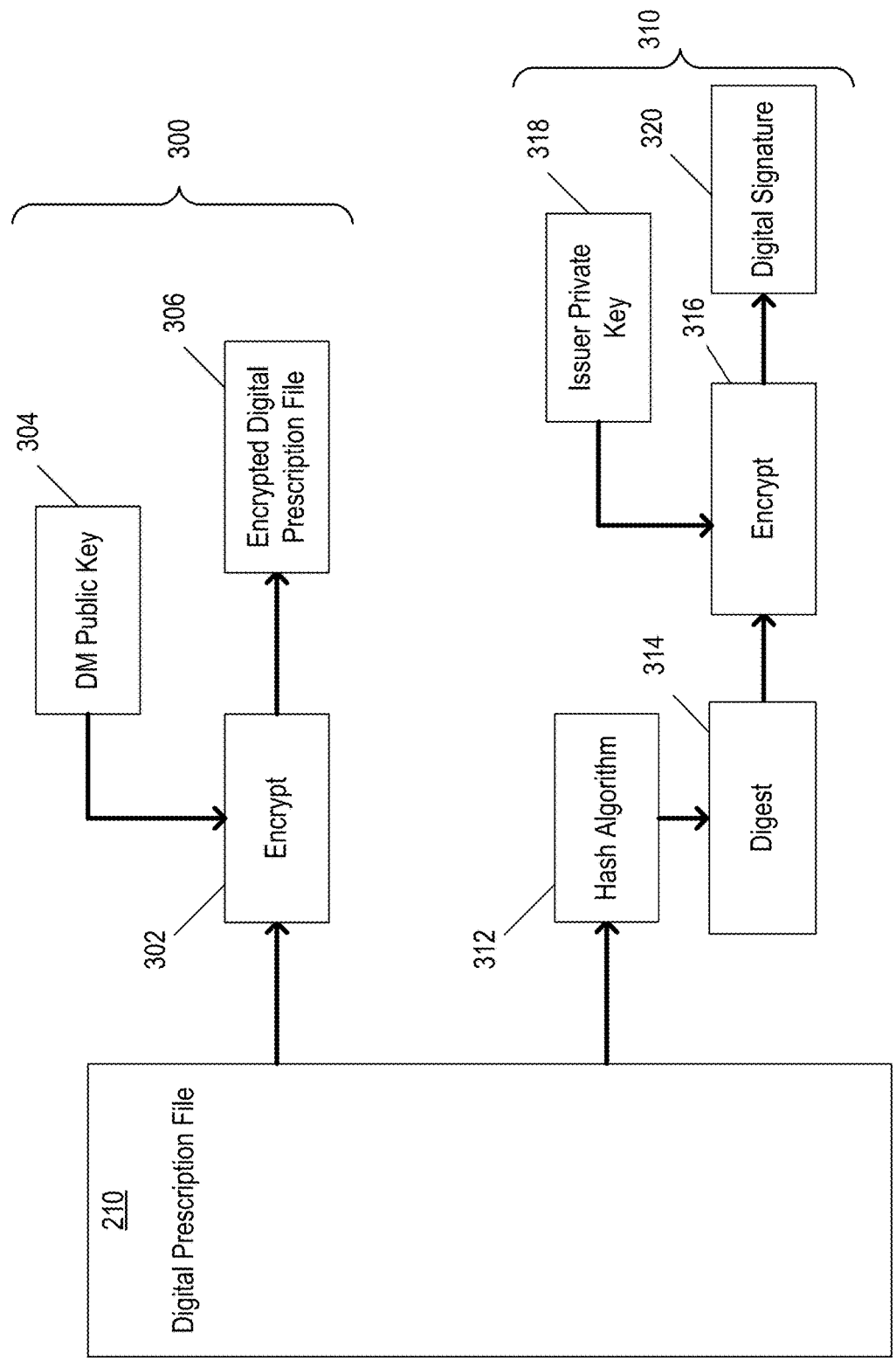
FIG. 3A illustrates an example technique for encrypting and digitally signing the digital prescription file.

FIG. 3A shows an example of a technique that may be employed to encrypt 300 and digitally sign 310 a digital prescription file (e.g., the digital prescription file 210 of FIG. 2) for implementations in which the digital prescription file is encrypted.

As described above, the digital prescription file 210 includes a prescription in plaintext that defines one or more parameters of a dialysis treatment to be applied to the patient by the DM 102. The digital prescription file 210 may be prepared by an issuer (e.g., the issuer 204 of FIG. 2). The digital prescription file 210 may be encrypted using a cryptography system such as an asymmetric cryptography system, sometimes referred to as public-key cryptography. For example, the information included in the digital prescription file 210 may be encrypted 302 using a DM public key 304 that corresponds to the DM 102 (and, e.g., other related DMs). The information in the digital prescription file 210 is transformed into a different form according to a cryptographic algorithm that considers the DM public key 304, thereby resulting in an encrypted digital prescription file 306. The cryptographic algorithm may be based on a mathematical problem that admits no efficient solution. As a result of the encryption 302, the encrypted digital prescription file 306 may take the form of an alphanumeric code that is unintelligible on its face to anyone who may intercept the encrypted digital prescription file 306. Thus, the encryption 302 helps to ensure that the information contained in the digital prescription file 210 is kept confidential during transit.

The digital prescription file 210 is also digitally signed 310 by the issuer 204. When we say that data is "digitally signed," we mean that a digital signature has been appended to the data. A digital signature typically contains an encrypted digest of the data. As shown in FIG. 3A, the contents of the digital prescription file 210 are hashed according to a hash algorithm 312 in order to produce a digest 314. In some implementations, the hash algorithm 312 is a mathematical algorithm that is designed to be a one-way function (e.g., a function that is infeasible to invert). The digest 314 is then encrypted 316 using an issuer private key 318 that corresponds to the issuer 204, thereby creating a digital signature 320. The digital signature 320 and the encrypted digital prescription file 306 are then provided to the DM 102.

Figure 3B:
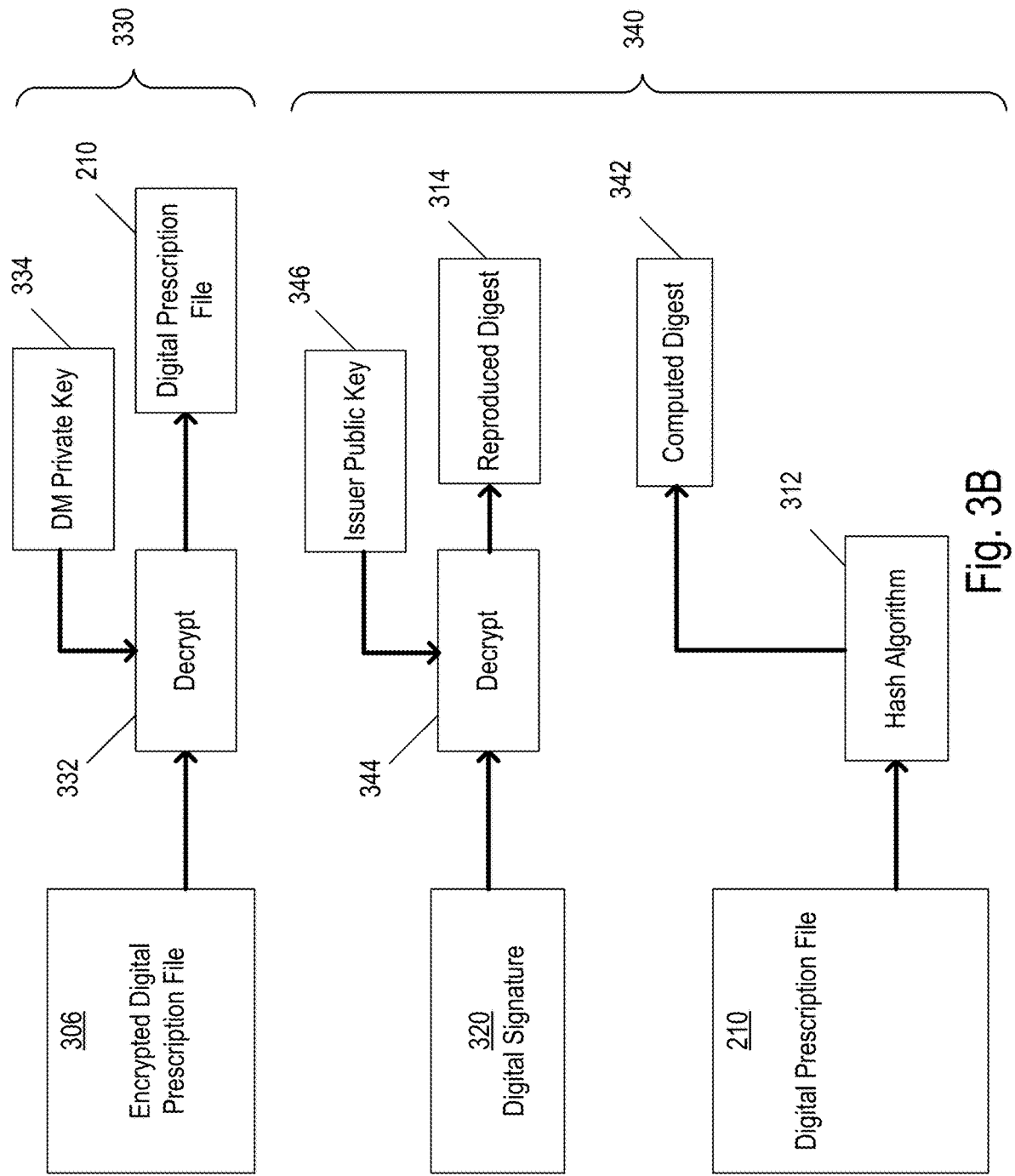
FIG. 3B illustrates an example technique for decrypting and checking the digital signature of the digital prescription file.

FIG. 3B shows an example of a technique that may be employed by the DM 102 to verify the digital signature 320 of the encrypted digital prescription file 306. In this example, the technique includes decrypting 330 the encrypted digital prescription file 306 and checking 340 the digital signature 320. In implementations in which the digital prescription file is not encrypted and therefore does not need to be decrypted, the decrypting 330 step can be omitted.

After receiving the encrypted digital prescription file 306 from the issuer 204, the DM 102 decrypts 332 the file using a DM private key 334 that corresponds to the DM public key 304. For example, the private key 334 can provide the information necessary for the cryptographic algorithm to convert the unintelligible alphanumeric code back into plaintext, thereby reproducing the original digital prescription file 210.

Because the digital prescription file 210 was encrypted using a public key (e.g., the DM public key 304), it is possible that someone who is not authorized to provide prescriptions may nonetheless obtain the DM public key 304 and provide an encrypted prescription to the DM 102. Thus, to ensure that the digital prescription file 210 comes from a trustworthy source and is safe to implement, the source of the digital prescription file (e.g., the issuer 204) can be verified by checking 340 the digital signature 320.

After the encrypted digital prescription file 306 is decrypted 332 to reproduce the plaintext contained therein, the plaintext is hashed according to the hash algorithm 312 to produce a computed digest 342. The digital signature 320, which includes an encrypted version of the digest 314, is decrypted 344 using an issuer public key 346 that corresponds to the issuer private key 318 in order to reproduce the digest 314. The computed digest 342 is then compared to the reproduced (e.g., decrypted) digest 314. If the computed digest 342 and the reproduced digest 314 are equal, it can be confirmed that the digital prescription file 210 was not modified since being digitally signed by the issuer 204, and the issuer 204 was the one who performed the signature operation. The steps of reproducing the digest, computing a digest using the hash algorithm 312, and comparing the reproduced digest 314 to the computed digest 342 are sometimes collectively referred to herein as verifying the digital signature 320.

As described above, there are multiple ways in which the DM 102 can obtain the issuer public key 346 in order to verify the digital signature 320. In some implementations, the DM 102 communicates with the CA (202 of FIG. 2) to obtain the issuer public key 346. For example, after decrypting the encrypted digital prescription file 306 and identifying the purported issuer 204, the DM 102 may ask the CA 202 whether the purported issuer 204 is authorized to provide prescriptions. If the purported issuer 204 is authorized to provide prescriptions, the CA 202 can provide the issuer public key 346 that corresponds to the issuer 204 who is known to be authorized. The DM 102 can use the issuer public key 346 to confirm that the digital prescription file 210 was in fact signed by the authorized issuer 204 and was not modified since being signed.

In some implementations, the DM 102 may obtain the issuer public key 346 directly from the issuer 204. For example, along with the encrypted digital prescription file 306, the issuer 204 may provide an issuer certificate (208 of FIG. 2) to the DM 102 that includes the issuer public key 346 and which is signed by the CA 202 using the CA private key 209. A CA certificate (214 of FIG. 2) that is stored on the DM 102 includes the CA public key 216 that corresponds to the CA private key 209. The digital signature on the issuer certificate 208 can be verified by the DM 102 using the CA public key 216. If the digital signature is verified, it is confirmed that the issuer certificate 208 was unmodified since being signed by the CA 202, and the CA 202 was the one who performed the signature operation. Because the CA 202 is a trusted entity, the DM 102 can treat the information included in the issuer certificate 208 (e.g., the issuer public key 206) as trusted. The DM 102 may then use the issuer public key 206 included in the issuer certificate 208 to verify the digital signature accompanying the encrypted digital prescription file 306. In this way, in some implementations, the DM 102 can confirm that the issuer 204 is authorized to provide prescriptions without the DM 102 ever knowing the actual identity of the issuer 204.

In some implementations, the digital prescription file 210 and the issuer certificate 208 may be provided to the DM 102 using a portable storage medium. For example, the digital prescription file 210 and the issuer certificate 208 may be uploaded to the DM 102 from a portable memory device such as a USB flash drive. In some examples, the digital prescription file 210 is digitally signed and encrypted before it is uploaded to the USB flash drive. The USB flash drive can be inserted into a USB port of the DM 102 and the digital prescription file 210 can be uploaded. The DM 102 can then decrypt the digital prescription file 210 and verify the digital signature. In this way, a communications network need not be used to deliver the digital prescription file 210.

Accordingly, providing the digital prescription file 210 via a USB flash drive may be beneficial for situations in which the DM 102 does not have access to the network (110 of FIG. 1) and/or the Internet. As described above, using only the DM private key 212 and the information contained in the digital prescription file 210, the issuer certificate 208, and the CA certificate 214, the DM 102 may confirm that the issuer 204 is an authorized issuer (e.g., authorized to provide prescriptions) and also decrypt the digital prescription file 210 to obtain the prescription for implementing on the DM 102. Verification of the authorized status of the issuer 204 can be performed without concurrent communication with the CA 202.

While certain implementations have been described, other implementations are possible.

While the DM private key and the CA certificate have been described as being stored on the dialysis machine, in some implementations, the DM private key and the CA certificate may be stored in another location that is accessible by the DM. For example, the DM private key and the CA certificate may be stored on a server that is accessible by the DM via the network.

In some implementations, CA certificate may be updated periodically. For example, the CA certificate and/or the CA public key contained therein may be updated according to a planned rotation over time. The dialysis machine may replace a current version of the CA certificate and/or the CA public key with an updated version that can subsequently be used to check the CA signature on issuer certificates.

While the dialysis machine has been described as communicating with remote entities through the network, in some implementations, the dialysis machine is configured to communicate directly with remote entities. For example, the transceiver may be configured to facilitate a direct connection between the dialysis machine and a remote entity, such as an issuer of a digital prescription file and/or a certificate authority.

While the systems and techniques described herein have been largely described with reference to a dialysis machine, and in particular, a PD machine, other types of medical treatment systems and/or machines may also use the systems and techniques to transmit digital prescription files and verify the validity of the digital prescription files and their issuers. Examples of other medical treatment systems that may employ the techniques described herein include hemofiltration systems, hemodiafiltration systems, apheresis systems, cardiopulmonary bypass systems, and hemodialysis ("HD") systems. In some implementations, the medical treatment system is a dialysis machine configured for use at a patient's home (e.g., a home dialysis machine ("HDM")). The HDM can take the form of a home PD machine or a home hemodialysis ("HD") machine.

Figure 4:
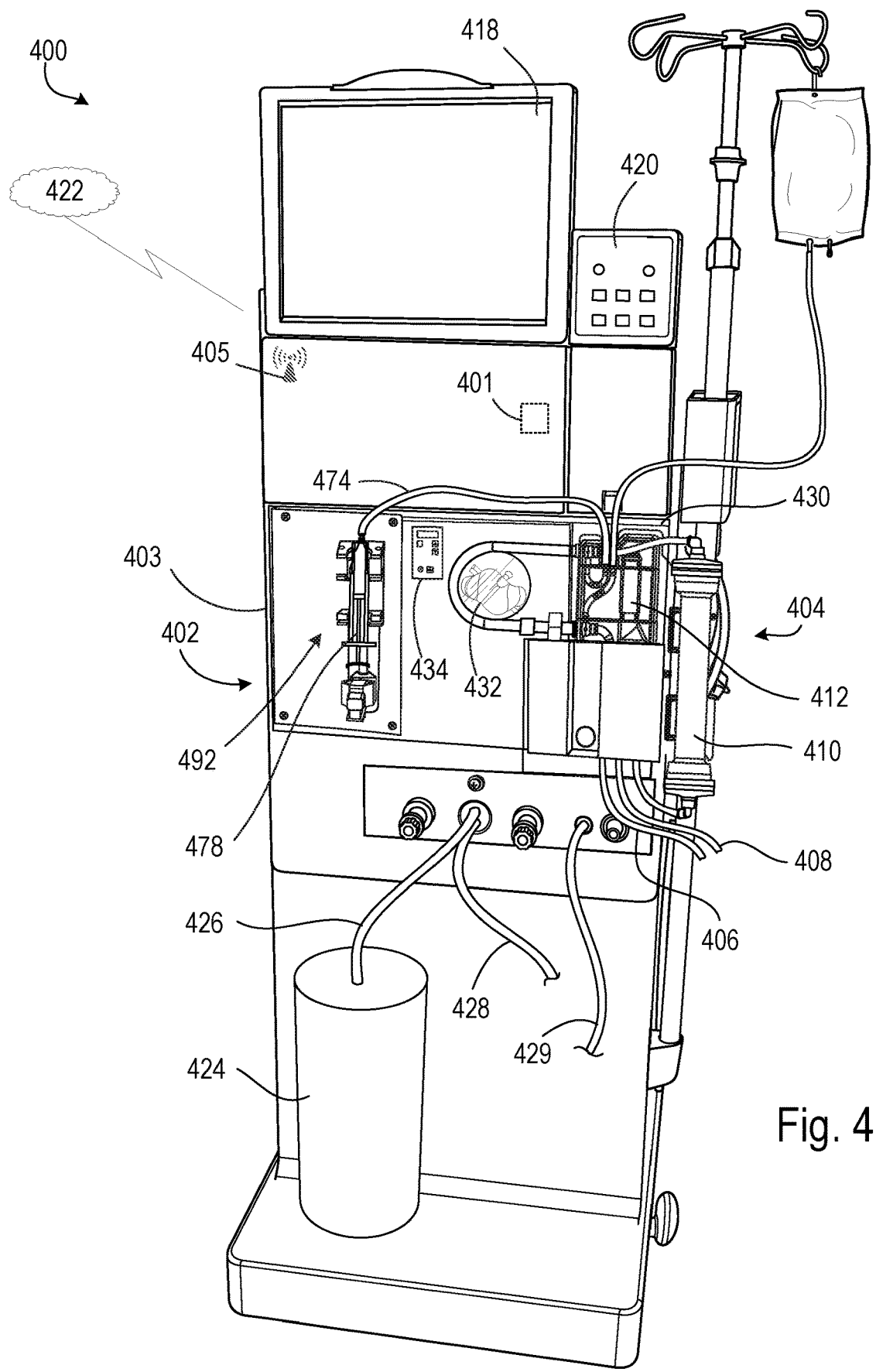
FIG. 4 is a front perspective view of a hemodialysis machine that is connected to a network.

FIG. 4 shows an HD system 400 that is configured to receive a digital prescription file in a manner similar to that described above. In some implementations, the HD system 400 is configured for use at a patient's home (e.g., a home HD system). The HD system 400 includes an HD machine 402 to which a disposable blood component set 404 that forms a blood circuit is connected. During hemodialysis, arterial and venous patient lines 406, 408 of the blood component set 404 are connected to a patient and blood is circulated through various blood lines and components, including a dialyzer 410, of the blood component set 404. At the same time, dialysate is circulated through a dialysate circuit formed by the dialyzer 410 and various other dialysate components and dialysate lines connected to the HD machine 402. Many of these dialysate components and dialysate lines are located inside the housing 403 of the HD machine 402, and are thus not visible in FIG. 4. The dialysate passes through the dialyzer 410 along with the blood. The blood and dialysate passing through the dialyzer 410 are separated from one another by a semi-permeable structure (e.g., a semi-permeable membrane and/or semi-permeable microtubes) of the dialyzer 410. As a result of this arrangement, toxins are removed from the patient's blood and collected in the dialysate. The filtered blood exiting the dialyzer 410 is returned to the patient. The dialysate that exits the dialyzer 410 includes toxins removed from the blood and is commonly referred to as "spent dialysate." The spent dialysate is routed from the dialyzer 410 to a drain.

One of the components of the blood component set 404 is an air release device 412. The air release device 412 includes a self-sealing vent assembly that allows air to pass through while inhibiting (e.g., preventing) liquid from passing through. As a result, if blood passing through the blood circuit during treatment contains air, the air will be vented to atmosphere as the blood passes through the air release device 412.

As shown in FIG. 4, a dialysate container 424 is connected to the HD machine 402 via a dialysate supply line 426. A drain line 1428 and an ultrafiltration line 429 also extend from the HD machine 402. The dialysate supply line 426, the drain line 428, and the ultrafiltration line 429 are fluidly connected to the various dialysate components and dialysate lines inside the housing 403 of the HD machine 402 that form part of the dialysate circuit. During hemodialysis, the dialysate supply line 426 carries fresh dialysate from the dialysate container 424 to the portion of the dialysate circuit located inside the HD machine 402. As noted above, the fresh dialysate is circulated through various dialysate lines and dialysate components, including the dialyzer 410, that form the dialysate circuit. As the dialysate passes through the dialyzer 410, it collects toxins from the patient's blood. The resulting spent dialysate is carried from the dialysate circuit to a drain via the drain line 428. When ultrafiltration is performed during treatment, a combination of the spent dialysate and excess fluid drawn from the patient is carried to the drain via the ultrafiltration line 429.

The blood component set 404 is secured to a module 430 attached to the front of the HD machine 402. The module 430 includes a blood pump 432 capable of driving blood through the blood circuit. The module 430 also includes various other instruments capable of monitoring the blood flowing through the blood circuit. The module 430 includes a door that when closed, as shown in FIG. 4, cooperates with the front face of the module 430 to form a compartment sized and shaped to receive the blood component set 404. In the closed position, the door presses certain blood components of the blood component set 404 against corresponding instruments exposed on the front face of the module 430. Such an arrangement facilitates control of the flow of blood through the blood circuit and monitoring of the blood flowing through the blood circuit.

The blood pump 432 can be controlled by a blood pump module 434. The blood pump module 434 includes a display window, a start/stop key, an up key, a down key, a level adjust key, and an arterial pressure port. The display window displays the blood flow rate setting during blood pump operation. The start/stop key starts and stops the blood pump 432. The up and down keys increase and decrease the speed of the blood pump 432. The level adjust key raises a level of fluid in an arterial drip chamber.

A drug pump 492 also extends from the front of the HD machine 402. The drug pump 492 is a syringe pump that includes a clamping mechanism configured to retain a syringe 478 of the blood component set 404. The drug pump 492 also includes a stepper motor configured to move the plunger of the syringe 478 along the axis of the syringe 478. A shaft of the stepper motor is secured to the plunger in a manner such that when the stepper motor is operated in a first direction, the shaft forces the plunger into the syringe 478, and when operated in a second direction, the shaft pulls the plunger out of the syringe 478. The drug pump 492 can thus be used to inject a liquid drug (e.g., heparin) from the syringe 478 into the blood circuit via a drug delivery line 474 during use, or to draw liquid from the blood circuit into the syringe 478 via the drug delivery line 474 during use.

The HD machine 402 includes a touch screen 418 and a control panel 420. The touch screen 418 and the control panel 420 allow an operator to input various treatment parameters to the HD machine 402 and to otherwise control the HD machine 402. In addition, the touch screen 418 serves as a display. The touch screen 418 functions to provide information to the patient and the operator of the HD system 400. For example, the touch screen 418 may display information related to a dialysis treatment to be applied to the patient, including information related to a prescription, as described above.

The HD machine 402 includes a processing module 401 that resides inside the machine and which is configured to communicate with the touch screen 418 and the control panel 420. The processing module 401 is configured to receive data from the touch screen 418 and the control panel 420 and control the HD machine 402 based on the received data. For example, the processing module 401 can adjust the operating parameters of the HD machine 402.

The HD machine 402 is configured to connect to a network 422. The HD machine 402 includes a transceiver 405 that is configured to facilitate the connection to the network 422. Other medical devices (e.g., peripheral devices or monitors, other dialysis machines, etc.) may be configured to connect to the network 422 and communicate with the HD machine 402. Similarly, one or more remote entities, such as issuers of digital prescription files and/or authority services tasked with verifying identities of issuers and certifying ownership of public keys corresponding to the issuers, may be able to connect to the network 422 and communicate with the HD machine 402 in order to provide digital prescriptions for implementing on the HD machine 402, digital certificates, and/or public keys usable to check digital signatures, as described above.

Figure 5:
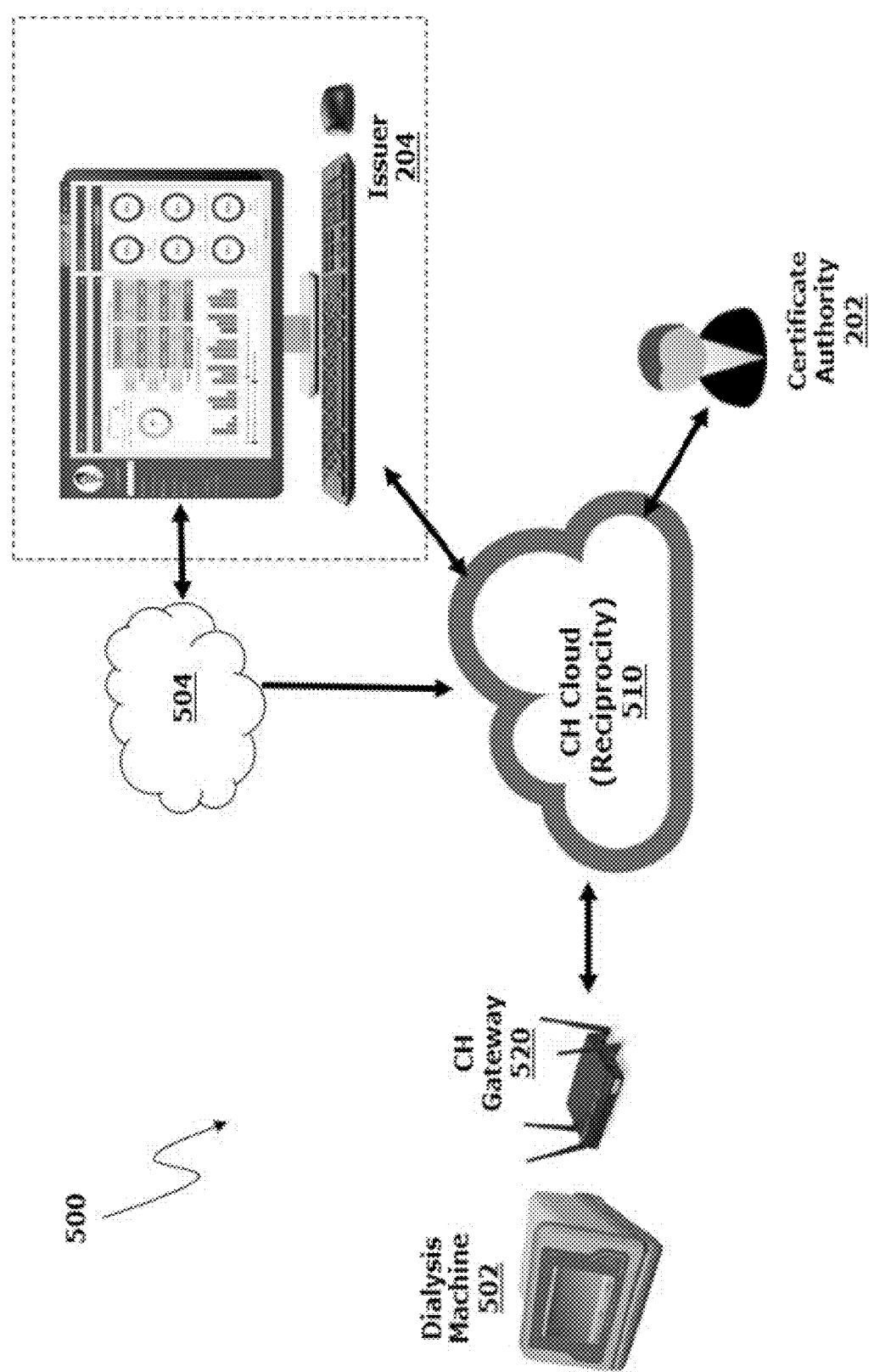
FIG. 5 is a schematic illustration showing an example of a Connected Health Service ("CHS") system.

In some implementations, a dialysis machine (DM) 502 (e.g., like the PD machine 102 of FIG. 1 and/or the HD machine 402 of FIG. 4) is configured to communicate with the certificate authority (e.g., the CA 202 of FIG. 2) and/or the issuer (e.g., the issuer 204 of FIG. 2) through a connected system (e.g., via the network 110 of FIG. 1 and/or the network 422 of FIG. 4). FIG. 5 is a schematic illustration showing an example of a Connected Health Service ("CHS") 500 system that can include, among other things, a CH Cloud 510 and a CH Gateway 520, which collectively may also be referred to as Reciprocity. The CH Cloud 510 may be a cloud-based application that serves as a communication pipeline (e.g., facilitates the transfer of data) among components of the CHS system 500. The CH Gateway 520 may serve as a communication device (e.g., a standard communication device) among dialysis machines that are part of the CHS system 500. The CH Gateway 520 is in communication with the DM 502 and the CH Cloud 510 and is configured to receive data from the CH Cloud 510 and provide the data to the DM 502. In some examples, the digital prescription file 210 is encrypted and then uploaded to the CH Cloud 510. In some implementations, the digital prescription file 210 may be checked for compatibility and/or otherwise processed by a processing system 504 that may be part of the system of the issuer 204 and/or provided by an Internet or cloud-based system before being uploaded to the CH Cloud 510. The DM 502 may poll the CH Cloud 510 for available files (e.g., via the CH Gateway 520), and the DM 502 may temporarily store available files for processing. In situations in which multiple digital prescription files are available on the CH Cloud 510, the DM 502 may identify and implement newer digital prescription files (e.g., based on a date associated with the digital prescription file).

Such date identification can allow the DM 502 to implement up-to-date prescriptions (e.g., the most up-to-date prescriptions) associated with the particular patient. The patient may then follow a patient confirmation process to accept the digital prescription file 210 before the prescription data is programmed into the DM 502 for implementation.

In some implementations, the CH Cloud 510 may include a component that acts as a proxy for performing digital signature operations. For example, the issuer 204 may communicate with the CH Cloud 510 to authenticate itself. Upon verification of the identity of the issuer 204, the CH Cloud 510 may confirm that it has access to the issuer private key and perform the digital signature operation on behalf of the issuer 204.

The communication between the DM 502 and the CA 202 and/or the issuer 204 may be secured according to one or more cryptographic protocols. For example, Transport Layer Security ("TLS") may be employed to provide communications security over the network 110, 422. TLS can provide privacy and data integrity between the DM 502 and the CA 202 and/or the issuer 204. In some implementations, TLS employs encryption according to one or more standards, such as the Advanced Encryption Standard ("AES"). In some implementations, other data besides the digital prescription file 210 may be exchanged among the components of the CHS system 500, including treatment data and/or device maintenance data transmitted between the DM 502 and the issuer 204.

In some implementations, Reciprocity is an application and services platform that enables medical device service providers (e.g., dialysis service providers) and patients (e.g., dialysis patients) to easily exchange data electronically through the lifecycle of care. The Reciprocity ecosystem may be segregated into three major areas. The first area may be the home space where a patient can receive their dialysis treatment (e.g., at the dialysis machine 502). With a combination of device agents and a gateway connection (e.g., the CH Gateway 520), the patient can download new prescription and configuration files, wirelessly integrate biometric vital measurements into their treatment, and/or upload critical treatment data to the cloud (e.g., CH Cloud 510). The second area is a series of backend business and data processing services (e.g., the processing system 504) built onto the latest Internet of Things (IoT) platform technologies. The cloud (e.g., the CH Cloud 510) may be the communication hub and delivery system for Reciprocity. The cloud facilitates the capturing, storing, and/or publishing out of both treatment and device data files. The third area is the integration application and services used with service providers (e.g., the issuer 204 the CA 202). The integration application and services allow service providers to create and manage prescriptions and/or configurations without incorporating the required logic to properly check for compatibility or format for a targeted device.

Figure 6:
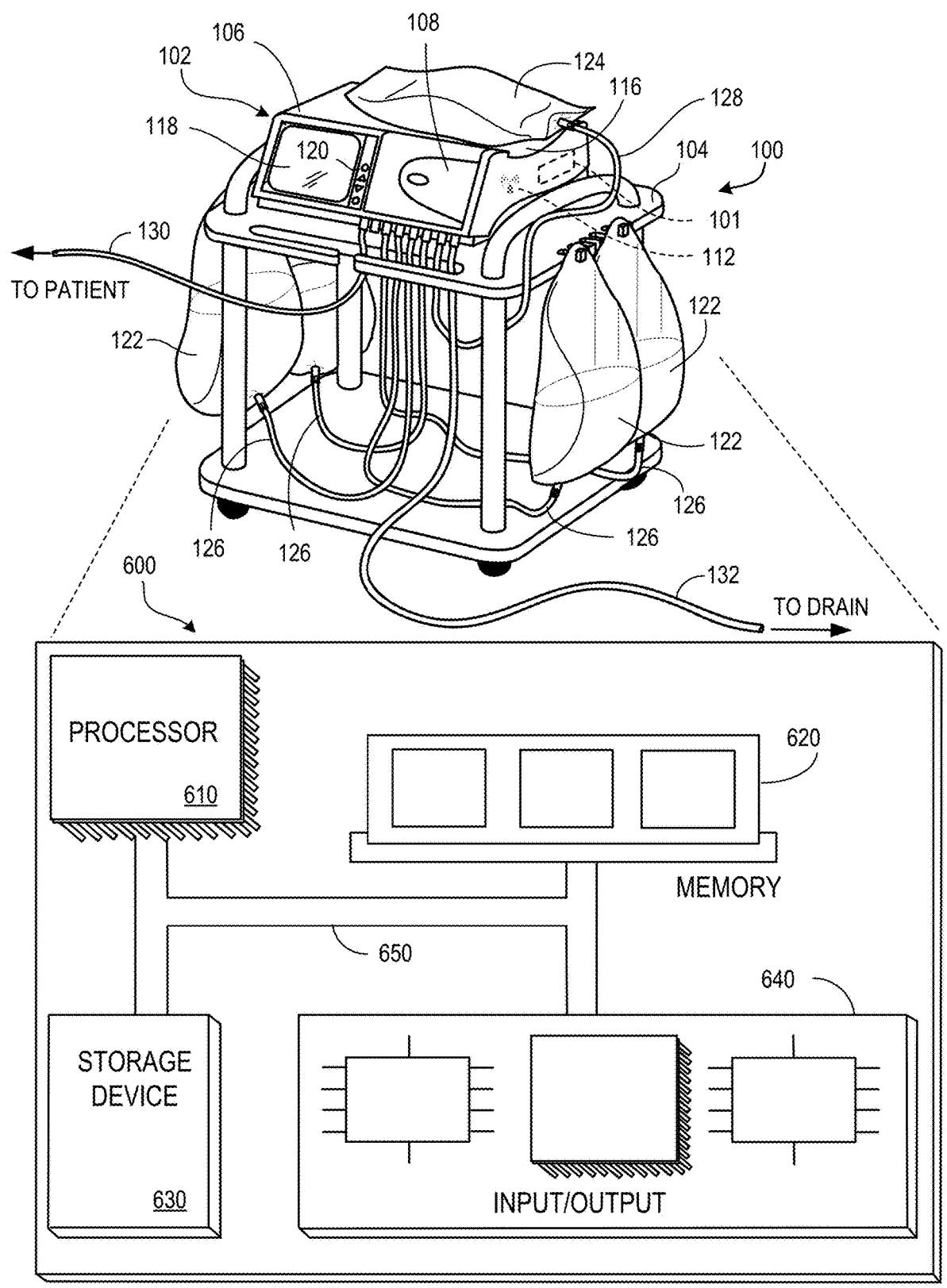
FIG. 6 is a block diagram of an example computer system.

FIG. 6 is a block diagram of an example computer system 600. For example, referring to FIGS. 1 and 4, the processing modules 101, 401 could be examples of the system 600 described here. The system 600 includes a processor 610, a memory 620, a storage device 630, and an input/output device 640. Each of the components 610, 620, 630, and 640 can be interconnected, for example, using a system bus 650. The processor 610 is capable of processing instructions for execution within the system 600. The processor 610 can be a single-threaded processor, a multi-threaded processor, or a quantum computer. The processor 610 is capable of processing instructions stored in the memory 620 or on the storage device 630. The processor 610 may execute operations such as causing the dialysis system to carry out functions related to a dialysis treatment according to a prescription received in a digital prescription file.

The memory 620 stores information within the system 600. In some implementations, the memory 620 is a computer-readable medium. The memory 620 can, for example, be a volatile memory unit or a non-volatile memory unit. In some implementations, the memory 620 stores information related to patients' identities. In some implementations, the memory 620 stores information related to issuers and/or certificate authorities, such as certificates and/or public keys that correspond to particular issuers and/or certificate authorities. In some implementations, the memory 620 stores a private key that corresponds to the dialysis machine (e.g., the DM private key).

The storage device 630 is capable of providing mass storage for the system 600. In some implementations, the storage device 630 is a non-transitory computer-readable medium. The storage device 630 can include, for example, a hard disk device, an optical disk device, a solid-date drive, a flash drive, magnetic tape, or some other large capacity storage device. The storage device 630 may alternatively be a cloud storage device, e.g., a logical storage device including multiple physical storage devices distributed on a network and accessed using a network. In some implementations, the information stored on the memory 620 can also or instead be stored on the storage device 630.

The input/output device 640 provides input/output operations for the system 600. In some implementations, the input/output device 640 includes one or more of network interface devices (e.g., an Ethernet card), a serial communication device (e.g., an RS-232 10 port), and/or a wireless interface device (e.g., a short-range wireless communication device, an 802.11 card, a 3G wireless modem, or a 4G wireless modem). In some implementations, the input/output device 640 includes driver devices configured to receive input data and send output data to other input/output devices, e.g., a keyboard, a printer, and display devices (such as the touch screen 118, 418). In some implementations, mobile computing devices, mobile communication devices, and other devices are used.

In some implementations, the system 600 is a microcontroller. A microcontroller is a device that contains multiple elements of a computer system in a single electronics package. For example, the single electronics package could contain the processor 610, the memory 620, the storage device 630, and input/output devices 640.

Although an example processing system has been described in FIG. 6, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of implementations of the invention have been described. Nevertheless, it will be understood that various modifications may be made without departing from the spirit and scope of the invention. Accordingly, other implementations are within the scope of the following claims.

What is claimed is:

1. A method comprising:
   connecting with a portable memory device that stores (i) a digital prescription file that is encrypted and digitally signed by an issuer of the digital prescription file before being uploaded to the portable memory device, and (ii) a certificate associated with the issuer, wherein the digital prescription file is encrypted using a first public key, without the issuer knowing an identity of a medical treatment machine, and wherein the digital prescription file is digitally signed by the issuer using an issuer private key that corresponds to the issuer;
   receiving, from the portable memory device, by the medical treatment machine, the digital prescription file and the certificate;
   decrypting the digital prescription file using a first private key that corresponds to the first public key, wherein the first private key is accessible by the medical treatment machine;
   identifying the issuer of the digital prescription file using the decrypted digital prescription file;
   determining that the issuer of the digital prescription file is an authorized issuer by verifying that the certificate including an issuer public key that corresponds to (i) the issuer, and (ii) the issuer private key used to digitally sign the digital prescription file, is digitally signed by a trusted authority service; and
   verifying a digital signature on the digital prescription file using the issuer public key that corresponds to the authorized issuer to confirm that the issuer is the authorized issuer,
   wherein the issuer is confirmed to be the authorized issuer without the medical treatment machine knowing an identity of the issuer.

2. The method of claim 1, wherein the first private key that corresponds to the first public key is pre-loaded on the medical treatment machine.

3. The method of claim 1, wherein the issuer public key that corresponds to the authorized issuer is provided by the trusted authority service.

4. The method of claim 3, wherein the trusted authority service is a certificate authority.

5. The method of claim 1, comprising performing a dialysis treatment based on the digital prescription file.

6. The method of claim 1, wherein the digital prescription file is encrypted by the issuer without the issuer knowing additional information about the medical treatment machine.

7. The method of claim 6, wherein the digital prescription file is decrypted by the medical treatment machine before the medical treatment machine learns the identity of the issuer.

8. The method of claim 1, comprising:
   receiving, by the medical treatment machine, the certificate that corresponds to the issuer, wherein the certificate is digitally signed by the trusted authority service using a private key that corresponds to the trusted authority service; and
   verifying a digital signature on the certificate using a public key that corresponds to the trusted authority service to confirm that the issuer public key included in the certificate corresponds to an authorized issuer.

9. The method of claim 8, comprising determining that the trusted authority service is trusted to verify identities of issuers and certify ownership of issuer public keys corresponding to the issuers.

10. The method of claim 9, wherein a certificate that includes a public key that corresponds to the trusted authority service is stored in the medical treatment machine.

11. The method of claim 9, wherein a certificate that includes a public key that corresponds to the trusted authority service is received by the medical treatment machine in a manner that indicates that the trusted authority service is a trusted authorizer of prescription issuers.

12. The method of claim 8, wherein the certificate that corresponds to the issuer is provided by the trusted authority service after the trusted authority service verifies the identity of the issuer and certifies that the issuer is an authorized issuer.

13. A method comprising:
   connecting with a portable memory device that stores (i) a digital prescription file that is encrypted and digitally signed by an issuer of the digital prescription file before being uploaded to the portable memory device, and (ii) a certificate associated with the issuer, wherein the digital prescription file is encrypted using a first public key, without the issuer knowing an identity of a medical treatment machine, and wherein the digital prescription file is digitally signed by the issuer using an issuer private key that corresponds to the issuer;

receiving, from the portable memory device, by the medical treatment machine, the digital prescription file and the certificate;

wherein the certificate includes an issuer public key that corresponds to the issuer, wherein the certificate is digitally signed by a trusted authority service using an authority private key that corresponds to the trusted authority service;

decrypting the digital prescription file using a first private key that corresponds to the first public key, wherein the first private key is accessible by the medical treatment machine;

verifying a digital signature on the certificate using an authority public key that corresponds to the trusted authority service to confirm that the issuer public key included in the certificate corresponds to an authorized issuer; and verifying a digital signature on the digital prescription file using the issuer public key included in the certificate to confirm that the issuer is the authorized issuer, wherein the issuer is confirmed to be the authorized issuer without the medical treatment machine knowing an identity of the issuer.

14. The method of claim 13, wherein the issuer is confirmed to be the authorized issuer without the medical treatment machine knowing additional information about the issuer.

15. A medical system comprising:
a medical device;
data storage; and
a processor configured for:
connecting with a portable memory device that stores a digital prescription file that is encrypted and digitally signed by an issuer of the digital prescription file before being uploaded to the portable memory device, and (ii) a certificate, wherein the digital prescription file is encrypted using a first public key, wherein the digital prescription file is digitally signed by the issuer using an issuer private key that corresponds to the issuer;

receiving, from the portable memory device, the digital prescription file and the certificate;

decrypting the digital prescription file using a first private key that corresponds to the first public key, wherein the first private key is accessible by the medical device;

identifying the issuer of the digital prescription file using the decrypted digital prescription file;

determining that the issuer of the digital prescription file is an authorized issuer by verifying that the certificate including an issuer public key that corresponds to i) the issuer, and ii) the issuer private key used to digitally sign the digital prescription file, is digitally signed by a trusted authority service; and verifying a digital signature on the digital prescription file using the issuer public key that corresponds to the authorized issuer to confirm that the issuer is the authorized issuer, wherein the issuer is confirmed to be the authorized issuer without the medical device knowing an identity of the issuer.

16. The medical system of claim 15, wherein the medical device is a dialysis machine that is configured to perform a dialysis treatment based on the digital prescription file.

17. The medical system of claim 16, wherein the dialysis machine comprises a home dialysis machine ("HDM").

18. The medical system of claim 16, wherein the dialysis machine comprises a peritoneal dialysis ("PD") machine.

19. The medical system of claim 16, wherein the dialysis machine comprises a hemodialysis ("HD") machine.

* * * * *